United States Patent [19]
Goto et al.

[11] Patent Number: 5,362,704
[45] Date of Patent: Nov. 8, 1994

[54] HERBICIDAL TETRAZOLINONES

[75] Inventors: Toshio Goto, Shimotsuga; Seishi Ito, Tochigi; Yukiyoshi Watanabe, Saitama; Shin-ichi Narabu, Ibaraki; Akihiko Yanagi, Oyama, all of Japan

[73] Assignee: Nihon Bayer Agrochem K.K., Tokyo, Japan

[21] Appl. No.: 201,927

[22] Filed: Feb. 24, 1994

[30] Foreign Application Priority Data

Feb. 25, 1993 [JP] Japan ................................. 5-59395

[51] Int. Cl.$^5$ ................ C07D 257/04; A01N 43/713; A01N 47/38
[52] U.S. Cl. ..................... 504/134; 504/136; 504/139; 504/261; 548/253
[58] Field of Search ............. 504/261, 134, 136, 139; 548/253

[56] References Cited

U.S. PATENT DOCUMENTS

| | | | |
|---|---|---|---|
| 4,618,365 | 10/1986 | Covey et al. | 71/92 |
| 4,826,529 | 5/1989 | Covey et al. | 71/92 |
| 4,830,661 | 5/1989 | Covey et al. | 71/92 |
| 5,003,075 | 3/1991 | Covey et al. | 548/251 |
| 5,019,152 | 5/1991 | Covey et al. | 71/92 |
| 5,136,868 | 8/1992 | Theodoridis | 71/92 |

FOREIGN PATENT DOCUMENTS 0146279 2/1988 European Pat. Off. .

OTHER PUBLICATIONS

Pestic. Sci., 1990, vol. 30, pp. 259–274.
1987 British Crop Protection Conference-Weeds, pp. 249–255.
Bell et al., "A QSAR Study of Substituted Tetrazolinone Herbicides", 1987 British Crop Protection Conference-Weeds.

*Primary Examiner*—Richard L. Raymond
*Assistant Examiner*—S. Mark Clardy
*Attorney, Agent, or Firm*—Sprung Horn Kramer & Woods

[57] ABSTRACT

Herbicidal novel tetrazolinones of the formula

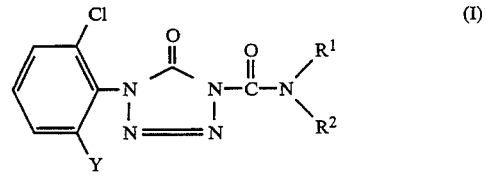

(I)

wherein
Y represents hydrogen, chlorine, or methyl,
$R^1$ represents ethyl or n-propyl, and
$R^2$ represents cyclopentyl or cyclohexyl, with the proviso that the total of the carbon atoms of $R^1$ and $R^2$ is 7 or 8. They may be mixed with other herbicides.

18 Claims, No Drawings

HERBICIDAL TETRAZOLINONES

The present invention relates to novel tetrazolinones, to a process for the preparation thereof, and to their use as paddy-herbicides.

It has already been disclosed that tetrazolinone derivatives have herbicidal properties (see U.S. Pat. Nos. 4,956,469, 5,003,075 and 5,019,152 or the corresponding European Applications EP-A-146,279 and EP-A-202,929).

There have now been found novel tetrazolinones of the formula (I)

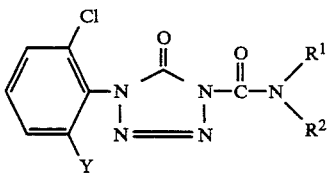

wherein
Y represents hydrogen, chlorine, or methyl,
$R^1$ represents ethyl or n-propyl, and
$R^2$ represents cyclopentyl or cyclohexyl, with the proviso that the total of the carbon atoms of $R^1$ and $R^2$ is 7 or 8.

The compounds of the formula (I) can be obtained by a process in which compounds of the formula (II)

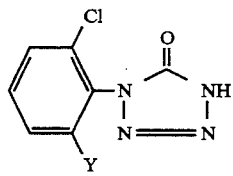

are reacted with compounds of the formula (III)

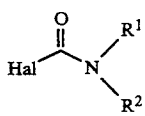

wherein
Hal is an eliminating group such as chlorine, bromine, or the like,
in the presence of an inert solvent and, if appropriate, in the presence of an acid binder.

The novel tetrazolinones (I) exhibit powerful herbicidal properties, in particular against paddy-field weeds.

While the compounds of the formula (I), according to the invention, fall within the scope of the aforementioned U.S. and EP patents, the compounds of the formula (I) have not been specifically disclosed therein. And, surprisingly, the compounds of the formula (I) exhibit a substantially much greater herbicidal action against paddy-weeds than those specifically known from the references.

Among the compounds of the formula (I), according to the invention, preferred compounds are those in which
Y represents hydrogen or methyl.

Specifically, the following compounds, in addition to the compounds mentioned in the Examples, are noted:

1-(2-chlorophenyl)-4-(N-cyclopentyl-N-ethylcarbamoyl)-5(4H)-tetrazolinone,
1-(2-chlorophenyl)-4-(N-cyclopentyl-N-n-propylcarbamoyl)-5(4H)-tetrazolinone,
1-(2-chlorophenyl)-4-(N-cyclohexyl-N-ethylcarbamoyl)-5(4H)-tetrazolinone,
1-(2-chloro-6-methylphenyl)-4-(N-cyclopentyl-N-n-propylcarbamoyl)-5(4H)-tetrazolinone, and
1-(2-chloro-6-methylphenyl)-4-(N-cyclohexyl-N-ethylcarbamoyl)-5(4H)-tetrazolinone.

If use is made, in the above-recited process, of 1-(2-chlorophenyl)-5(4H)-tetrazolinone and N-cyclohexyl-N-ethylcarbamoyl chloride, as the starting materials for example, the reaction can be expressed by the following reaction equation:

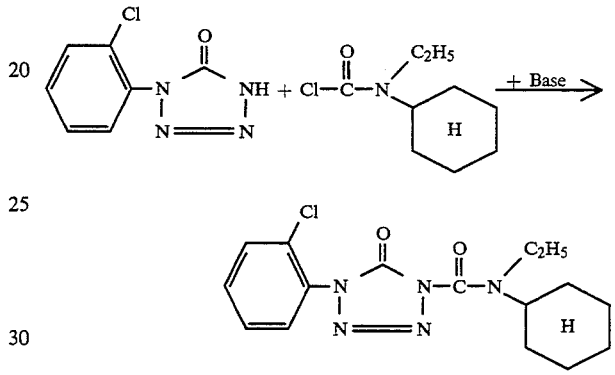

The starting compounds of formula (II) can be prepared in the manner similar to that described in "The Journal of Organic Chemistry", Vol. 45, No. 21, 1980, pages 5130–5136 or "The Journal of American Chemical Society", Vol. 81, No. 7, 1980, pages 3076–3079.

As examples of compounds of formula (II), there may be mentioned the following:
1-(2-chlorophenyl)-5(4H)-tetrazolinone,
1-(2-chloro-6-methylphenyl)-5(4H)-tetrazolinone, and
1-(2,6-dichlorophenyl)-5(4H)-tetrazolinone.

The compounds of formula (III) are well known in the field of organic chemistry. As specific examples thereof, there may be mentioned:
N-cyclopentyl-N-ethylcarbamoyl chloride,
N-cyclopentyl-N-n-propylcarbamoyl chloride, and
N-cyclohexyl-N-ethylcarbamoyl chloride.

In carrying out the process mentioned above, use may be made, as suitable diluents, of any inert organic solvents.

Examples of such diluents are aliphatic, cycloaliphatic and aromatic, optionally chlorinated, hydrocarbons such as pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like; ethers such as diethyl ether, methyl ethyl ether, diisopropyl ether, dibutyl ether, dioxane, dimethoxyethane (DME), tetrahydrofuran (THF), diethylene glycol dimethyl ether (DGM) and the like; nitriles such as acetonitrile, propionitrile and the like; acid amides such as dimethyl formamide (DMF), dimethyl acetamide (DMA), N-methylpyrrolidone, 1,3-dimethyl-2-imidazolidinone, hexamethylphosphoric triamide (HMPA) and the like; sulfones and sulfoxides such as dimethyl sulfoxide (DMSO), sulfolane and the like; and bases such as pyridine.

The above-mentioned process may be carried out in the presence of an acid binder such as for example, inorganic bases including hydroxides, carbonates, bicarbonates, alcoholates, and hydrides of alkali metals, such as sodium hydrogen carbonate, potassium hydrogen carbonate, sodium carbonate, potassium carbonate, lithium hydroxide, sodium hydroxide, potassium hydroxide, calcium hydroxide, sodium methoxide, potassium methoxide, potassium tert-butoxide, lithium hydride, sodium hydride, potassium hydride, and the like; inorganic amides of alkali metals such as lithium amide, sodium amide, potassium amide and the like; and organic bases including tertiary amines, dialkylaminoanilines and pyridines, such as triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), 1,8-diazabicyclo[5,4,0]-undec-7-ene (DBU) and the like. Furthermore, there may be used organic lithium compounds such as, for example, methyl lithium, n-butyl lithium, sec-butyl lithium, tert-butyl lithium, phenyl lithium, dimethyl copper lithium, lithium diisopropyl amide, lithium cyclohexylisopropyl amide, lithium dicyclohexyl amide, n-butyl lithium.-DABCO, n-butyl lithium.DBU, n-butyl lithium.TMEDA and the like.

In the above-mentioned process the reaction temperature can be varied within a substantially wide range. In general, the reaction is carried out at a temperature of from about −30° C. to about 200° C., preferably from about −20° C. to about 130° C.

Further, the reaction is preferably carried out under normal pressure, although it is also possible to employ a higher or reduced pressure.

When the above-mentioned process is carried out, use may be made, for example, of 1.0 to 1.2 mols of the compound of the formula (III) in a diluent such as acetonitrile, for example, per mol of the compound of the formula (II) in the presence of 1 to 1.2 molar amount of an acid binder to obtain the desired compound.

The compounds represented by the general formula (I) according to the present invention can be used as herbicides for controlling paddy weeds.

Further, it has been discovered that a specially high herbicidal activity can be exhibited by herbicidal mixed compositions comprising, as active components, the compounds represented by the general formula (I) according to the present invention, together with at least one of the members selected from the group consisting of herbicidally active sulfonamides, herbicidally active pyrazols, herbicidally active propionanilides, herbicidally active triazines, herbicidally active carbamates, herbicidally active diphenylethers, and herbicidally active acid amides.

Surprisingly, the herbicidal mixed compositions according to the present invention have been found to exhibit herbicidal effects substantially higher than the sum of the herbicidal effects that can be exhibited individually by the herbicidally active, respective components and, as the result, the concentration of each of the active compounds can be substantially reduced when practicing weed control operations, while at the same time, a wide herbicidal spectrum can be obtained. Further, the herbicidal compositions according to the present invention have been found to expand the period of possible application, for example, in paddy rice cultivation, and exhibit excellent herbicidal effects for a period of from the early stage of weed-emergence to the weed-growing stage, with prolonged duration of activity and excellent residual effect, as well as phytotoxicity-free, excellent herbicidal effects on rice plants.

As specific examples of the herbicidal sulfonamides to be employed in the present herbicidal mixed compositions there may be mentioned, for example, N-2-biphenylylsulfonyl N'-(4,6-dimethoxy-1,3,5-triazin-2-yl) urea, ethyl 5-[3-(4,6-dimethoxypyrimidin-2-yl)ureidosulfonyl]-1-methylpyrazole-4-carboxylate, methyl 2-[3-(4,6-dimethoxypyrimidin-2-yl)ureidosulfonylmethyl]benzoate, 3-(4,6-dimethoxy-1,3,5-triazin -2-yl)-1-[2-(2-methoxyethoxy)-phenylsulfonyl]urea, N-(2-chloroimidazole [1,2-a]pyridin-3-yl-sulfonyl)-N'-(4,6-dimethoxy-2-pyrimidyl) urea, N'-(4,6-dimethoxypyrimidin-2-yl)-N''-(4-methylphenylsulfonylamino)-N'''-(4-ethoxycarbonyl-1-methylpyrazol-5-yl-sulfonyl) guanidine, and N-(2-cyclopropylcarbonylphenylsulfamoyl)-N'-(4,6-dimethoxypyridin-2-yl) urea.

The above-mentioned compounds are also well known in the art (see Japanese Patent Publication No. 481/1984, Japanese Patent Laid-open Nos. 112379/1982, 56452/1982, 122488/1984, 38091/1989 and 70475/1989).

As specific examples of the herbicidally active pyrazoles to be employed in the present invention there may be mentioned, for example, 4-(2,4-dichlorobenzoyl)-1,3-dimethylpyrazol-5-yl-p-toluenesulfonate, 2-[4-(2,4-dichlorobenzoyl)-1,3-dimethylpyrazol-5-yl]acetophenone, and 2-[4-(2,4-dichloro-m-toluoyl)-1,3-dimethylpyrazol-5-yloxy]-4-methylacetophenone.

As specific examples of the propionailides to be employed in the present invention there may be mentioned, for example, 2-(β-naphthyloxy)propionanilide, and (RS)-2-(2,4-dichloro-m-tolyloxy)propionanilide.

As specific examples of the herbicidally active triazines to be employed in the present invention there may be mentioned, for example, 2,4-bis(ethylamino)-6-(methylamino)-1,3,5-triazine, and 2-ethylamino-4-(1,2-dimethylpropylamino)-6-methylthio-1,3,5-triazine.

As specific examples of the herbicidally active carbamates there may be mentioned, for example, S-p-chlorobenzyl diethylthiocarbamate, S-1-methyl-1-phenylethyl piperidine-1-carbothioate, and S-benzyl 1,2-dimethylpropyl(ethyl)thiocarbamate.

As examples of the herbicidally active diphenylethers to be employed in the present invention there may be mentioned, for example, 2,4,6-trichlorophenyl-4'-nitrophenylether, and 2,4-dichlorophenyl-3'-methoxy-4'-nitrophenylether.

As examples of the herbicidally active acid amides to be employed in the present invention there may be mentioned, for example (RS)-2-bromo-N-(α,α-dimethylbenzyl)-3,3-dimethylbutylamide.

The above-mentioned active compounds are known to be herbicidally active and are disclosed in "Pesticide Manual", 1991, published by The British Crop Protect Council.

In the herbicidal mixed compositions according to the present invention, the mixing weight ratio of the active components may be varied over a relatively wide range.

In general, use may be made, per one part by weight of the compounds represented by the general formula (I), of the herbicidal sulfonamides in an amount from 0.01 to 2 parts by weight, preferably from 0.05 to 1 part by weight; the herbicidally active pyrazoles in an amount of from 2.5 to 35 parts by weight, preferably from 3 to 15 parts by weight; the herbicidally active propionanilides in an amount of from 0.6 to 50 parts by weight, preferably from 2.0 to 28 parts by weight; the herbicidally active triazines in an amount of from 0.06 to 10 parts by weight, preferably from 0.15 to 6 parts by weight; the herbicidally active carbamates in an amount of from 3 to 15 parts by weight, preferably from 5 to 10 parts by weight; the herbicidally active diphenylethers in an amount of from 5 to 35 parts by weight, preferably from 7 to 15 parts by weight; and the herbicidally active acid amides in an amount of from 3.5 to 25 parts by weight, preferably from 4.0 to 10 parts by weight, respectively.

The mixed compositions according to the present invention exhibit a strong herbicidal activity; therefore the above-mentioned compositions may be used as herbicidal compositions and they may be advantageously used particularly as selective herbicidal compositions for paddy rice.

The herbicidal agents and mixed compositions according to the present invention can be applied, for example, to the following paddy weeds:

Dicotyledons of the following genera: Polygonum, Rorippa, Rotala, Lindernia, Bidens, Dopatrium, Eclipta, Elatine, Gratiola, Lindernia, Ludwigia, Oenanthe, Ranunculus, Deinostema.

Monocotyledons of the following genera: Echinochloa, Panicum, Poa, Cyperus, Monochoria, Fimbristylis, Sagittaria, Eleocharis, Scirpus, Alisma, Aneilema, Blyxa, Eriocaulon, Potamogeton.

The herbicidal agents and mixed compositions according to the present invention can be applied specifically, for example, to the following paddy weeds in paddy fields:

| Botanical names | Latin names |
|---|---|
| Dicotyledons | |
| Rotala indica | Rotala indica Koehne |
| False pimpernel | Lindernia Procumbens Philcox |
| False loosestrife | Ludwigia prostrata Roxburgh |
| Largeleaf pondweed | Potamogeton distinctus A. Benn |
| American waterwort | Elatine triandra Schk |
| Dropwort | Oenanthe javanica |
| Monocotyledons | |
| Barnyard grass | Echinochloa oryzicola vasing |
| Monochoria | Monochoria vaginalis Presl |
| Matsubai | Eleocharis acicularis L. |
| Water chestnut | Eleocharis Kuroguwai Ohwi |
| Umbrella plant | Cyperus difformis L. |
| Mizugayatsuri | Cyperus serotinus Rottboel |
| Urikawa | Sagittaria pygmaea Miq |
| Narrowleaf waterplantain | Alisma canaliculatum A. Br. et Bouche |
| Bulrush | Scirpus juncoides Roxburgh |

However, the application of the herbicidal agents and mixed compositions according to the present invention is not limited to the above-mentioned weeds, but the application can be effected likewise also to other lowland weeds inhabiting paddy fields.

The present herbicidal agent and mixed compositions can be incorporated into any conventional formulations. As the formulations may be mentioned, for example, a liquid agent, an emulsion, a hydrated agent, a suspension, a powdery agent, a soluble powdery agent, a granular agent, a suspended emulsion, and microcapsules in a polymeric substance.

Those preparations can be prepared through well-known processes. The processes can be effected, for example, by mixing the active compounds with an extender, namely, with a liquid diluent and/or a solid diluent and, if required, with a surfactant, namely, with an emulsifier and/or dispensant and/or a foaming agent.

In case of using water as an extender, for example, an organic solvent can also be used as an auxiliary solvent. As liquid diluents there my be mentioned, for example, aromatic hydrocarbons (such as xylene, toluene or alkylnaphthalene etc.), chlorinated aromatic or chlorinated aliphatic hydrocarbons (such as chlorobenzenes, ethylene chlorides or methylene chloride etc.), aliphatic hydrocarbons [such as cyclohexane etc.) or paraffins (for example, mineral-oil fractions, mineral or vegetable oils)], alcohols (such as butanol, glycol and ethers and esters thereof etc.), ketones (such as acetone, methyl ethyl ketone, methyl isobutyl ketone or cyclohexanone etc.), strong polar solvents (such as dimethylformamide and dimethyl sulfoxide etc.), and water can also be mentioned as a liquid diluent.

As solid diluents there may be mentioned ammonium salts, and natural soily minerals (such as kaolin, clay, talc, chalk, quartz, attapulgite, montmorillonite, or diatomite etc.) and soil synthetic minerals (such as highly diapersable silicic acid, alumina, silicate etc.). As solid carriers for granular agents there can be mentioned powdered and fractionated rocks (such as calcite, marble, pumice stone, meerschaum, dolomite etc.), synthetic grains of organic or inorganic powders, and fine particles of organic substances (such as saw dust, coconut-shells, corn ear-stems, and tobacco stalks etc.).

As emulsifiers and/or foaming agents three may be mentioned nonionic and anionic emulsifiers such as, for example, polyoxyethylene fatty acid esters, polyoxyethylene fatty alcohol ethers such as, for example, alkylaryl polyglycol ethers, alkyl sulfonates, alkyl sulfates, aryl sulfonates, etc., and albumin hydrolyzates.

As dispersants, for example, lignin-sulfite waste liquor and methyl cellulose are suitable.

Adhesives or stickers may also be used in the formulations in the form of a powdery agent, granular agent, jambo agent, or emulsion, and as adhesives or stickers there may be mentioned carboxymethyl cellulose, natural and synthetic polymers (such as gum arabic, polyvinyl alcohol, and polyvinyl acetate etc. for example), natural phosphatides (such as cephalins and lecithins), and synthetic phosphatides. Further as additives there may also be used mineral and vegetable oils.

Colorants may also be used, and as such colorants there may be mentioned inorganic pigments (such as, for example, iron oxide, titanium oxide and Prussian blue), and organic dyes such as, for example, alizarin dyes, azo dyes, and metallic phthalocyanine pigments, and further trace amounts of such materials as salts of iron, manganese, boron, copper, cobalt, molybdenum and zinc.

The formulation contains generally 0.1 to 95% by weight, preferably 0.5 to 90% by weight of the active compound.

In order to control weeds, the active compounds of the herbicidal agent and herbicidal composition according to the present invention can be used as such, or in the form of formulations thereof, and the mixture can be handled in the form of formulations or in the form of a tank-mixture.

The active compound according to the present invention can be used as a mixture with other well-known active compounds, that is, with active compounds normally used for paddy fields such as, for example, bactericides, insecticides, plant-growth regulators, plant nutritive agents, soil conditioners, safeners and any other herbicides.

To the herbicidal composition according to the present invention there may be added, per part by weight of the herbicidal sulfonamides, from 1 to 200 parts by weight, preferably from 2 to 100 parts by weight, of safener such as 1-($\alpha$,$\alpha$-dimethylbenzyl)-3-p-tolylurea, for example.

The present active compounds can be used as such, as their formulations or as the use forms prepared therefrom by further dilution thereof, such as in the forms of ready-to-use solutions, emulsions, suspensions, powders, wettable powders, pastes and granules.

They may be used in the customary manner, for example, by watering, spraying, atomizing, dusting, scattering, etc.

The present active compounds can be used either in the pre-, or post-emergence period of plants. It is also possible to apply the active compounds into soil before the seeds of plants are sown.

The concentration of active compound used in the present herbicidal agents can vary within a substantially wide range. It depends essentially on the nature of the desired effect. In general, the amounts used as a herbicide are from about 0.01 to about 10 kg of active compound per hectare, preferably from about 0.1 to about 2 kg/ha.

The dosages of the present herbicidal mixed compositions may be varied within a substantially wide range, viz., from 0.1 to 5 kg/ha and preferably from 0.2 to 3 kg/ha in terms of the amount of active compounds.

The preparation and the use of the active compounds according to the present invention are illustrated by the following examples. It should be noted that the scope of the invention is not limited only to the technical contents of the examples.

Synthesis Examples

Example 1

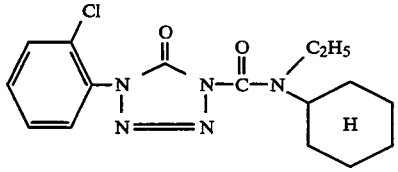 (3)

1-(2-chlorophenyl)-5(4H)-tetrazolinone (2 g) and potassium carbonate (1.68 g) were suspended in acetonitrile (30 ml), followed by fifteen minutes heating under refluxing. After cooling, N-cyclohexyl-N-ethylcarbamoyl chloride (2.31 g) was added to the reaction mixture, followed by a further five-hour heating under refluxing. The resulting mixture was filtered and the filtrate was evaporated under reduced pressure, and the resulting residue was subjected to flush column chromatography (hexane:ethylacetate=5:2), to obtain the desired 1-(2-chlorophenyl)-4-(N-cyclohexyl-N-ethylcarbamoyl)-5(4H)-tetrazolinone (3.02 g) having a m.p. in the range of from 77.5° to 79.5° C.

The compounds obtained by the above-mentioned reaction procedure, together with the compound obtained in Example 1, are shown in Table 1.

TABLE 1

| Compound No. | Y | $R^1$ | $R^2$ | physico-chemical data |
|---|---|---|---|---|
| 1 | H | $C_2H_5$ | cyclopentyl-H | $n_D^{20}$ 1.5585 |
| 2 | H | $C_3H_7$-n | cyclopentyl-H | m.p. 70 to 73.5° C. |
| 3 | H | $C_2H_5$ | cyclohexyl-H | m.p. 77.5 to 79.5° C. |
| 4 | $CH_3$ | $C_3H_7$-n | cyclopentyl-H | m.p. 92 to 93° C. |
| 5 | $CH_3$ | $C_2H_5$ | cyclohexyl-H | m.p. 71 to 74.5° C. |

Example 2 (Synthesis of Intermediate Compound)

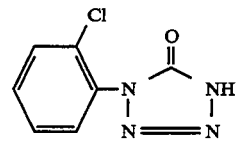

2-chlorophenylisocyanate (7 g) and trimethylsilylazide (7.9 g) were mixed and refluxed for eight hours. The excess trimethylsilylazide was distilled off under reduced pressure, and to the resulting residue there were added 40 ml of methanol. Thereafter, the solvent was distilled off under reduced pressure to give a crude product that was then subjected to flush column chromatography (hexane:ethylacetate=2:1), to obtain the desired 1-(2-chlorophenyl)-5(4H)-tetrazolinone (7 g) having a melting point in the range of from 124.5° to 125.5° C.

Biotest Example

Comparative compound

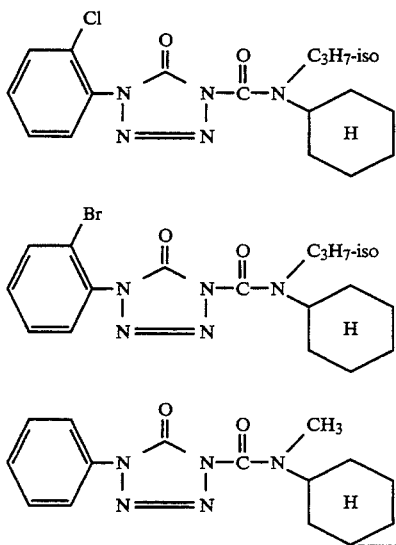

C-1

C-2

C-3

(C-1, C-2 and C-3 are similar to the compounds disclosed in Japanese Patent Application Disclosure No. Sho-60-146879 )1985)).

Test Example 3(Biotest Example)

Test on herbicidal activity against lowland weeds.

Formulation of Active Compounds

Carrier: 5 parts by weight of acetone

Emulsifier: 1 part by weight of benzyloxy polyglycol ether.

To produce a suitable preparation of each of the active compounds, 1 part by weight of an active compound was mixed with the stated amount of carrier and with the stated amount of emulsifier, and the resulting emulsifiable concentrate was then diluted with water to the desired concentrations.

Test Procedures

Aquatic paddy soil was filled in pots (1/2,000 ares, 25×20×9 cm), and rice seedlings (variety: Nipponbare) in the 2.5 leaf stage (plant height about 15 cm) were transplanted in two spots at a rate of three per hill.

Seeds of Echinochloa crus-galli P. B. var. oryzoides Ohwi, Cyperus difformis L., Scirpus juncoides Roxb., Monochoria vaginalis Presl., and annual broad-leaved weeds such as Lindernia pyxidaria L., Rotala indics Koehne, Elatine triandra Schk., Ammannia multiflora Roxb., Dopatrium junceum Hamilt. and so on were inoculated in the pots.

The soil in the pots was maintained in wet state. Two days after, each pot was watered to a depth of about 2 to 3 cm. Five days after the transplantation of the rice seedlings, a predetermined amount of the compounds in the form of an emulsion, prepared in the manner mentioned above was applied on the water-surface of each pot by means of a pipette.

After the treatment, each pot was maintained in the watered state to a depth of about 3 cm.

In the three week after the treatment, the herbicidal effect and the degree of phytotoxicity were evaluated, wherein 100% indicates the complete death and 0% indicates no herbicidal effect.

The results are shown in Table 2.

TABLE 2

| | Dosage of Active Compound (kg/ha) | Herbicidal effect (%) | | | | | Phytotoxicity (%) Rice Oryza |
|---|---|---|---|---|---|---|---|
| | | Echi-nochloa | Cyperus | Scirpus | Mono-choria | Broad leaf weeds | |
| Compound | | | | | | | |
| 2 | 0.3 | 100 | 100 | 100 | 100 | 100 | 5 |
| | 0.2 | 100 | 100 | 90 | 100 | 90 | 0 |
| 3 | 0.3 | 100 | 100 | 100 | 100 | 100 | 0 |
| | 0.2 | 100 | 100 | 90 | 100 | 90 | 0 |
| 4 | 0.3 | 100 | 100 | 100 | 100 | 100 | 0 |
| | 0.2 | 100 | 100 | 90 | 100 | 90 | 0 |
| 5 | 0.3 | 100 | 100 | 100 | 100 | 100 | 0 |
| | 0.2 | 100 | 100 | 90 | 100 | 80 | 0 |
| Comparative | | | | | | | |
| C-1 | 0.3 | 90 | 100 | 80 | 90 | 60 | 15 |
| | 0.2 | 80 | 90 | 70 | 80 | 50 | 10 |
| C-2 | 0.3 | 90 | 100 | 70 | 90 | 40 | 10 |
| | 0.2 | 60 | 90 | 40 | 60 | 30 | 5 |
| C-3 | 0.3 | 80 | 100 | 70 | 80 | 40 | 15 |
| | 0.2 | 60 | 80 | 40 | 50 | 30 | 10 |

Example 4 (Biotest)

Test for determining herbicidal effect of the present herbicidal compositions on lowland weeds.

In a greenhouse, aquatic paddy soil was filled in pots (1/2,000 ares, 25×20×9 cm), and rice seedlings (cv. Nipponbare) in the 2.5 leaf stage with a height of 15 cm were transplanted in two spots into the pot at a rate of three per hill.

Then, the tubers of Sagittaria pygmaea Miq and small pieces of Spikerrush (Eleocharis acicularis) as well as the seeds of the following respective weeds were inoculated into the respective pots and filled with water to a height of about 2 to 3 cm above the soil surface:

Echinochloa orizicola vasing,
Cyperus difformis L.,
Monochoria vaginalis Presl,
Broad leaved weeds such as Lindernia pyxidaria, Rotala indica Koehne, American waterwort (Elatine orientalis Makino), Ammannia multiflora Roxburgh, Dopatrium junceum Hamilton, Bulrush, Scirpus juncoides and Roxburgh.

Five days after the transplantation of the rice seedling, a predetermined amount of the active compounds in the form of an emulsion which had been prepared in the manner mentioned above, was applied on the water-surface of each pot. After that, water depth in each pot was maintained at about 3 cm.

Three weeks after application of the active compound, the herbicidal effect and the degree of phytotoxicity were determined according to the following rating system, wherein 100% indicates the complete death and 0% indicates no herbicidal effect.

The results are shown in the following Table 3:

In Table 3, A, B, C, D, E, F and G in the herbicidal compositions under test represent the following active compounds, respectively:

A: Methyl 2-[3-(4,6-dimethoxypyrimidin-2-yl)-ureidosulfonylmethyl]benzoate,
B: Ethyl 5-[3-(4,6-dimethoxypyrimidin-2-yl)-ureidosulfonyl]-1-methylpyrazole-4-carboxylate,
C: N-(2-chloroimidazole[1,2-a]pyridin-3-yl-sulfonyl)-N'-(4,6-dimethoxy-2-pyrimidyl)urea,
D: 4-(2,4-dichlorobenzoyl)-1,3-dimethyl-5-pyrazolyl-p-toluenesulfonate,
E: 2-(β-naphthyloxy)propionailide,
F: 2-ethylamino-4-(1,2-dimethyl propylamino)-6-methylthio-1,3,5-triazine,
G: S-p-chlorobenzyl diethylthiocarbamate.

and scope of the invention will suggest themselves to those skilled in the art.

We claim:

1. A tetrazolinone of the formula

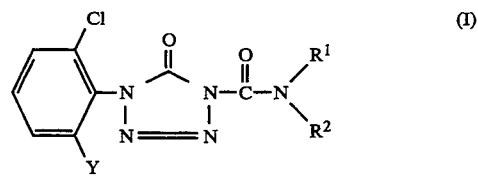

wherein
Y represents hydrogen, chlorine, or methyl,
R¹ represents ethyl or n-propyl, and
R² represents cyclopentyl or cyclohexyl, with the proviso that the total of the carbon atoms of R¹ and R² is 7 or 8.

2. A compound according to claim 1, wherein Y represents hydrogen or methyl.

3. A compound according to claim 1, wherein such compound is 1-(2-chlorophenyl)-4-(N-cyclohexyl-N-ethylcarbamoyl)-5(4H)-tetrazolinone of the formula:

TABLE 3

| Test Compound | Dosage of Active Compound (kg/ha) | Herbicidal Effect (%) | | | | | | Spikerrush (*Eleocharis acicularis*) | Phytotoxicity (%) Rice |
|---|---|---|---|---|---|---|---|---|---|
| | | Echi-nochloa | Cyperus | Mono-choria | Broad leaf weeds | Scirpus | Sagittaria | | |
| 1 + B | 0.10 + 0.021 | 100 | 100 | 100 | 100 | 100 | 100 | — | 0 |
| 2 + A | 0.10 + 0.075 | 100 | 100 | 100 | 100 | 100 | 100 | — | 0 |
| 3 + B | 0.10 + 0.021 | 100 | 100 | 100 | 100 | 100 | 100 | — | 0 |
| 4 + A | 0.10 + 0.075 | 100 | 100 | 100 | 100 | 100 | 100 | — | 0 |
| 4 + B | 0.10 + 0.021 | 100 | 100 | 100 | 100 | 100 | 100 | — | 0 |
| 4 + C | 0.10 + 0.09 | 100 | 100 | 100 | 100 | 100 | 100 | — | 0 |
| 3 + D | 0.10 + 1.8 | 100 | 100 | 100 | 100 | 100 | 100 | — | 0 |
| 5 + E | 0.10 + 2.1 | 100 | 100 | 100 | 100 | 100 | 100 | — | 0 |
| 4 + F | 0.10 + 0.33 | 100 | 100 | 100 | 100 | — | — | 100 | 0 |
| 4 + G(*1) | 0.10 + 1.5 | 100 | — | — | — | — | — | — | 0 |
| 1 | 0.10 | 80 | 100 | 80 | 80 | 60 | 0 | — | 0 |
| 2 | 0.10 | 70 | 100 | 80 | 90 | 70 | 0 | — | 0 |
| 3 | 0.10 | 80 | 100 | 80 | 90 | 70 | 0 | — | 0 |
| 4 | 0.10 | 80 | 100 | 80 | 90 | 70 | 0 | — | 0 |
| 5 | 0.10 | 70 | 100 | 80 | 90 | 70 | 0 | — | 0 |
| 4(*2) | 0.10 | 80 | — | — | — | — | — | — | 0 |
| A | 0.075 | 40 | 100 | 100 | 100 | 100 | 100 | — | 0 |
| B | 0.021 | 50 | 100 | 100 | 100 | 100 | 100 | — | 0 |
| C | 0.09 | 50 | 100 | 100 | 100 | 100 | 100 | — | 0 |
| D | 1.8 | 60 | 100 | 100 | 80 | 60 | 100 | — | 0 |
| E | 2.1 | 60 | 100 | 100 | 100 | 100 | 100 | — | 0 |
| F | 0.33 | 40 | 100 | 100 | 100 | — | — | 80 | 0 |
| G(*3) | 1.5 | 80 | — | — | — | — | — | — | 0 |

In Table 3, the composition indicated by (*1) controlled the emergence of Barnyard grass (Echinochloa) for a period of forty-eight days, while compound 4 indicated by (*2) controlled such emergence for a period of forty days, and compound G (*3) controlled such emergence for a period of twenty-five days.

Formulation Example 1

Water was added to a mixture consisting of 1 part by weight of the above-mentioned active compound 1, 0.25 parts by weight of the above-mentioned active compound A, 30 parts by weight of bentonite, 66.75 parts by weight of talc, and 2 parts by weight of lignin sulfonate, followed by an intimate kneading, granulating and drying to obtain granules.

It will be understood that the specification and examples are illustrative but not limitative of the present invention and that other embodiments within the spirit

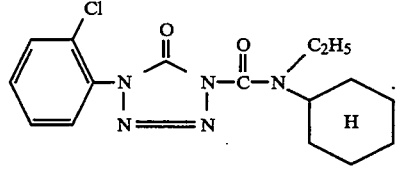

4. A compound according to claim 1, wherein such compound is 1-(2-chloro-6-methylphenyl)-4-(N-cyclopentyl-N-n-propyl-carbamoyl)-5(4H)-tetrazolinone of the formula:

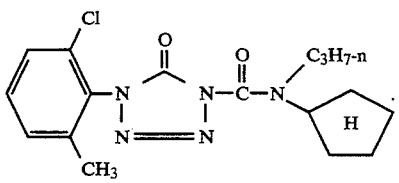

5. A compound according to claim 1, wherein such compound is 1-(2-chlorophenyl)-4-(N-cyclopentyl-N-ethyl-carbamoyl-5(4H)-tetrazolinone of the formula:

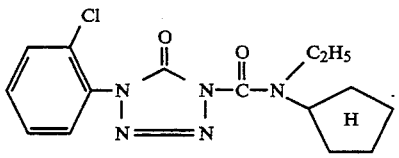

6. A compound according to claim 1, wherein such compound is 1-(2-chlorophenyl)-4-(N-cyclopentyl-N-n-propyl-carbamoyl)-5(4H)-tetrazolinone of the formula:

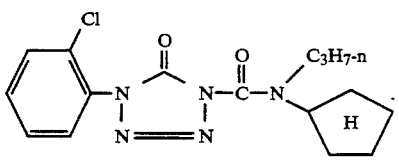

7. A compound according to claim 1, wherein such compound is 1-(2-chloro-6-methylphenyl)-4-(N-cyclohexyl-N-ethylcarbamoyl)-5(4H)-tetrazolinone of the formula:

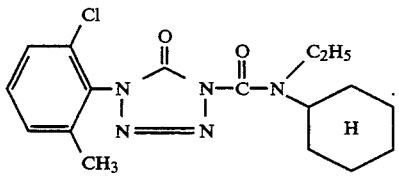

8. A herbicidal composition comprising a herbicidally effective amount of a compound according to claim 1 and a diluent.

9. A method of combatting unwanted vegetation which comprises applying thereto or to a locus from which it is desired to exclude such vegetation a herbicidally effective amount of a compound according to claim 1.

10. A herbicidal composition comprising a herbicidally effective amount of a compound according to claim 1 and as a further ingredient at least one compound selected from the group consisting of herbicidal sulfonamides, herbicidal pyrazoles, herbicidal propionanilides, herbicidal triazoles, herbicidal carbamates, herbicidal diphenylethers, and herbicidal acid amides.

11. A composition according to claim 10, wherein the further ingredient comprises
  N-2-biphenylylsulfonyl N'-(4,6-dimethoxy-1,3,5-triazin -2-yl)urea,
  ethyl 5-[3-(4,6-dimethoxypyrimidin -2-yl) ureidosulfonyl]-1-methylpyrazole-4-carboxylate,
  methyl 2-[3-(4,6-dimethoxypyrimidin -2-yl)ureidosulfonylmethyl]benzoate,
  3-(4,6-dimethoxy-1,3,5-triazin-2-yl)-1-[2-(2-methoxyethoxy)-phenylsulfonyl]urea,
  N-(2-chloroimidazole[1,2-a]pyridin-3-yl-sulfonyl)-N'-(4,6-dimethoxy-2-pyrimidyl)urea,
  N'-(4,6-dimethoxypyrimidin-2-yl)-N''-(4-methylphenylsulfonylamino)-N'''-(4-ethoxycarbonyl-1-methylpyrazol-5-yl-sulfonyl)guanidine, or
  N-(2-cyclopropylcarbonylphenylsulfamoyl)-N'-(4,6-dimethoxypyridin-2-yl)urea.

12. A composition according to claim 10, wherein the further ingredient comprises
  4-(2,4-dichlorobenzoyl)-1,3-dimethylpyrazol-5-yl-p-toluene sulfonate,
  2-[4-(2,4-dichlorobenzoyl)-1,3-dimethylpyrazol-5-yl]acetophenone, or
  2-[4-(2,4-dichloro-m-toluoyl)-1,3-dimethylpyrazol-5-yloxy]-4-methylacetophenone.

13. A composition according to claim 10, wherein the further ingredient comprises
  2-(β-naphthyloxy )propione anilide or
  (RS)-2-(2,4-dichloro-m-tolyloxy)propione anilide.

14. A composition according to claim 10, wherein the further ingredient comprises
  2,4-bis(ethylamino)-6-(methylamino)-1,3,5-triazine or
  2-ethylamino-4-(1,2-dimethylpropylamino)-6-methylthio-1,3,5-triazine.

15. A composition according to claim 10, wherein the further ingredient comprises
  S-p-chlorobenzyl diethylthiocarbamate,
  S-1-methyl-1-phenylethyl piperidine-1-carbothioate, or
  S-benzyl 1,2-dimethyl-propyl(ethyl)thiocarbamate.

16. A composition according to claim 10, wherein the further ingredient comprises
  2,4,6-trichlorophenyl-4'-nitrophenylether, or
  2,4-dichlorophenyl-3'-methoxy-4-nitrophenylether.

17. A composition according to claim 10, wherein the further ingredient comprises (RS)-2-bromo-N-(α,α-dimethylbenzyl)-3,3-dimethylbutylamide.

18. A compositions according to claim 10, wherein per part by weight of the tetrazolinone there is also present at least one of
  0.01 to 2 parts by weight of a herbicidal sulfonamide,
  2.5 to 35 parts by weight of a herbicidal pyrazole,
  0.6 to 50 parts by weight of a herbicidal propionanilide,
  0.06 to 10 parts by weight of a herbicidal triazine,
  3 to 15 parts by weight of a herbicidal carbamate,
  5 to 35 parts by weight of a herbicidal diphenylether, or
  3.5 to 25 parts by weight of a herbicidal amide.

* * * * *